United States Patent

Pilié et al.

[11] Patent Number: 5,606,111
[45] Date of Patent: Feb. 25, 1997

[54] APPARATUS AND METHOD FOR MEASUREMENT OF OFFGASSING RATE

[75] Inventors: Roland J. Pilié, Williamsville; Thomas M. McMahon, Hamburg; Michael D. Moskal, Depew, all of N.Y.

[73] Assignee: The United States of America as represented by the Secretary of the Army, Washington, D.C.

[21] Appl. No.: 547,473

[22] Filed: Oct. 24, 1995

[51] Int. Cl.⁶ .................................... G01N 7/14
[52] U.S. Cl. .......................................... 73/19.12
[58] Field of Search ..................... 73/19.01, 19.02, 73/19.04, 19.07, 19.12, 38, 864.33, 865.5

[56] References Cited

U.S. PATENT DOCUMENTS

| | | | |
|---|---|---|---|
| 4,112,739 | 9/1978 | Lyssy | 73/38 |
| 4,192,175 | 3/1980 | Godai et al. | 73/19.02 |

*Primary Examiner*—Michael Brock
*Attorney, Agent, or Firm*—Ulysses John Biffoni; Edward L. Stolarun

[57] ABSTRACT

A test cell apparatus and method for measuring gases emitted from a test sample. The apparatus having hollow, enclosed, gas impermeable chamber having side walls terminating at a closed end and a gas transfer end. The gas transfer end receives and emits a flow of a gas therethrough. The cell has a planar platform in the chamber extending from the closed end to the gas transfer end defining a first chamber portion including a first gas transfer end portion, and a second chamber portion including a second gas transfer end portion. The platform has an opening therethrough at a location proximate to the closed end of the chamber and a fan installed in it near the gas transfer end. Means are provided for fixing a test article through the platform such that part of the test article is positioned and exposed within the first chamber portion and another part of the test article is positioned and exposed within the second chamber portion. Means are provided for continuously moving a gas into the first gas transfer end portion, through the first chamber portion, over that part of the test article exposed within the first chamber portion, through the platform opening proximate to the closed end of the chamber, through the second chamber portion, over that part of the test article exposed within the second chamber portion, and out the second gas transfer end portion. Preferably the gas is recirculated from the second gas transfer end portion to the first gas transfer end portion. The testing apparatus is useful for measuring the offgasses emitted from a test sample.

19 Claims, 2 Drawing Sheets

```
AGENT                TEST CELL      ORIFICE      VACUUM PUMP
LADEN
AIR   ─────────→  [        ]  ──→ [      ]  ──→ [         ]  ─────────→  AGENT
IN                                      │                                 LADEN
                                        │                                 AIR TO
                                        ▼                                 HOOD
                                   TO MINICAMS
```

FIG. 2

APPARATUS AND METHOD FOR MEASUREMENT OF OFFGASSING RATE

GOVERNMENT INTEREST

The invention described herein may be manufactured, used and licensed by or for the United States Government.

BACKGROUND OF THE INVENTION

1. Field of the Invention

This invention relates generally to testing apparatus and more particularly to test cells for measuring the offgasses emitted from a test sample.

2. Description of the Prior Art

It is often desirable to measure the offgassing rate of sample articles to determine the potential exposure hazard to an unprotected person who must work in an area affected by agent vapors which evaporate from or desorb from a material. One method of testing articles is to deploy them within a wind tunnel and measuring emitted effluents. However, such an arrangement is only suitable for large test articles in special installations with elaborate equipment. Such an arrangement is impractical for laboratory scale or field testing. It would be desirable to produce a laboratory or field use scale test cell which could be used to measure the degassing rates of sample articles. According to the invention, measurements may be made by placing a test article material in the inventive test cell which accurately simulates the environmental conditions under which safe operation may be achieved, and measuring the rate at which agent vapors accumulate in the test cell. An ideal offgassing test procedure requires air flow over the test article to be equal to that encountered under real conditions. To standardize test procedures for test articles normally located out of doors, a flow rate of one meter per second over the test article is used. For reasons of safety, instrument sensitivity and economical operation, such a procedure had been heretofore considered unrealistic in ambient field conditions. The present invention accurately simulates field conditions and therefore permits accurate, safe, economical testing of small and medium size objects.

SUMMARY OF THE INVENTION

The invention provides a cell for measuring gases emitted by a test article. It comprises a hollow, enclosed, gas impermeable chamber having side walls terminating at a closed end and a gas transfer end. The gas transfer end is capable of receiving and emitting a flow of a ventilation gas therethrough. It has a planar platform positioned in the chamber extending from the closed end to the gas transfer end defining a first chamber portion including a first gas transfer end portion, and a second chamber portion including a second gas transfer end portion. The platform has an opening therethrough at a location proximate to the closed end of the chamber. Means are provided for fixing a test article through the platform such that part of the test article is positioned and exposed within the first chamber portion and another part of the test article is positioned and exposed within the second chamber portion. Means are provided for continuously moving a gas into the first gas transfer end portion, through the first chamber portion, over that part of the test article exposed within the first chamber portion, through the platform opening proximate to the closed end of the chamber, through the second chamber portion, over that part of the test article exposed within the second chamber portion, and out the second gas transfer end portion.

The invention also pertains to a method for measuring gases emitted by a test article which comprises providing the above hollow, enclosed, gas impermeable chamber. One then continuously moves a gas into the first gas transfer end portion, through the first chamber portion, over that part of the test article exposed within the first chamber portion, through the platform opening proximate to the closed end of the chamber, through the second chamber portion, over that part of the test article exposed within the second chamber portion, and out the second gas transfer end portion. In the preferred embodiment, gas continually recirculates over the test article to assure a complete mixing such that the concentration of desorbed vapor from the test article is uniform throughout the test cell. The effluent of ventilation gas from the second gas transfer end portion, which is then truly representative of the vapor concentration within the test cell, is then evaluated.

It is therefore an object of the invention to provide an improved test cell and method for measuring offgasses emitted from a test sample. It is a further object of the invention to provide a laboratory or field use scale test cell which can be used to measure the degassing rates of sample articles.

BRIEF DESCRIPTION OF THE DRAWINGS

FIG. 2 shows a schematic representation of an equipment configuration useful for determining the sorption coefficient.

DETAILED DESCRIPTION OF THE PREFERRED EMBODIMENT

Figure 1:
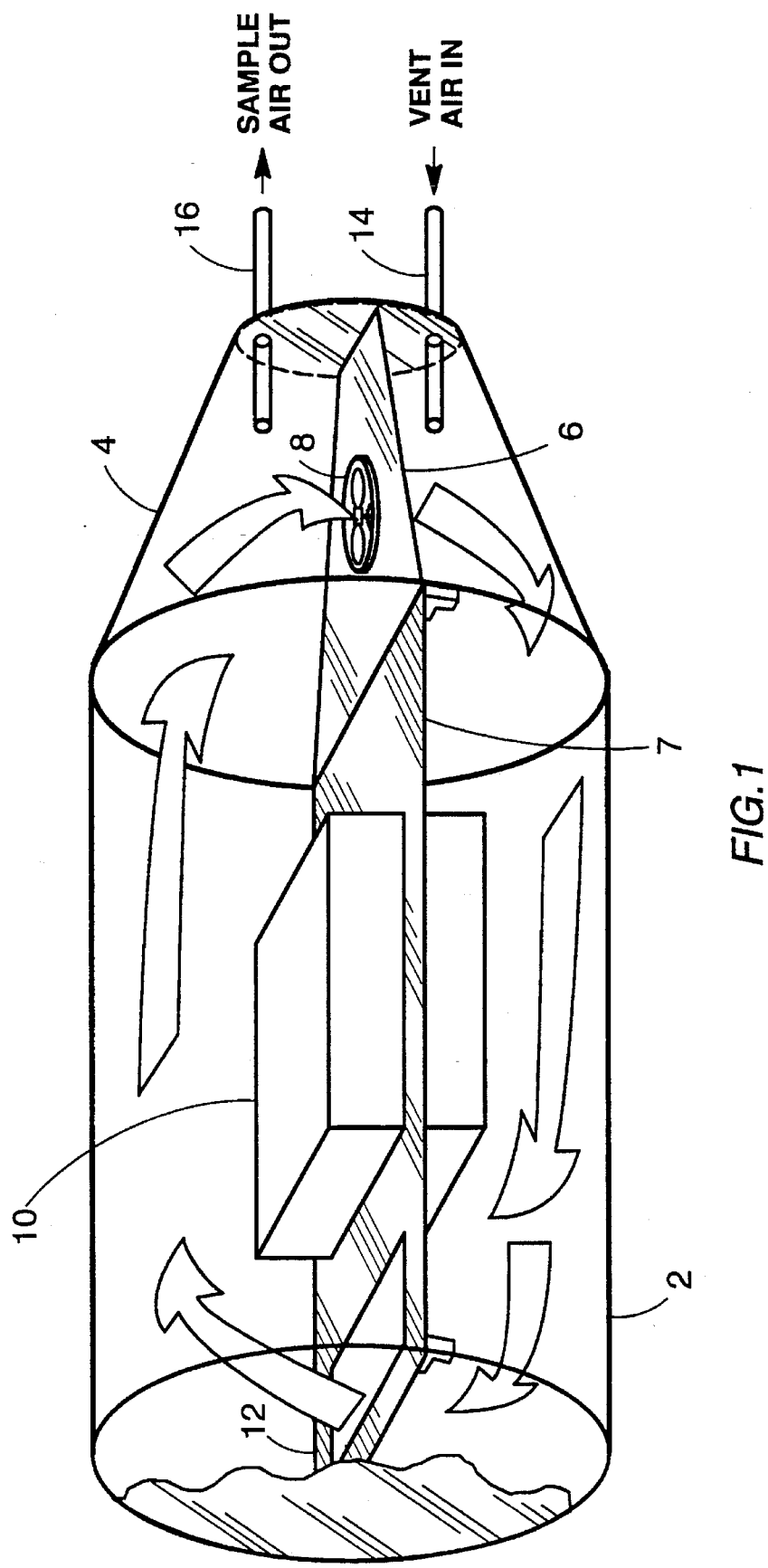
FIG. 1 shows a perspective cut-away view test cell according to the invention.

FIG. 1 shows a test cell according to the invention. It consists of a large diameter stainless steel cylinder 2 that is capped with a removable, truncated cone 4. The cone is bisected by a permanently mounted stainless steel plate 6. A second stainless steel plate or baffle 7, in which a slightly oversized profile of the test article has been removed, bisects the cylinder end and mates with plate 6. Plate 7 is preferably replaced with each test article. A controlled speed, DC muffin fan 8 is mounted in the plate 6 to provide air flow over a test article 10. The test article 10 is mounted by a fixture designed to hold it near the center of the test cell through the plate 7. The test cell supports the thin stainless steel plate 7 from which a test article profile has been removed. This plate, which is mated with the test article, bisects the test cell and serves to direct the air flow to a closed end 12 of the test cell. At the closed end, air that has flowed past one side of the test article passes through the open portion of baffle 7 and returns past the opposite side of the test article 10 and then to fan 8 for recirculation in the direction of the arrows. In the preferred embodiment, one should avoid direct contact between the test article and the plate with which it is mated, to avoid test article damage. A preferred test article to plate spacing is about ¼ inch. In the preferred embodiment as shown in FIG. 1, the test cell is a closed circuit wind tunnel of about 24 inches in diameter and about 36 inches long. Total volume of the unoccupied test cell is approximately 325 liters.

Provision is made to ventilate the test cell at a desired rate, for example, at one volumetric exchange per minute. Ambient air enters the test cell on the downwind side of the fan through entry port 14 and sample air removed from the upwind side of the fan through exit port 16. Power to the fan 8 may be adjusted to achieve the flow rate necessary to produce the desired windspeed through the most constricted region of the test section. For a determination of wind speed over the test object one may calibrate the fan using a hot wire anemometer inserted through an orifice provided for that purpose in the test cell. Volumetric flow rate can be determined as a function of power to the DC fan motor. The volumetric rate of flow of ventilation air exiting the test cell through exit port 16 may be measured by any suitable means. In the preferred embodiment, a laminar flow controller, not shown, may be used. Such a controller is available from Teledine Hastings of Hampton, Virginia.

Sample gas, such as ambient air containing test article effluent flowing through exit port 16, may be analyzed by any suitable means. The preferred analytical instrument, not shown, is a Miniature Chemical Agent Monitoring System (MiniCAMS™) which is available from CMS, Inc. of Alabama. The MiniCAMS is an automated gas chromatograph (GC) that is controlled by a computer. In use, sample air is drawn into the MiniCAMS test cell with an external vacuum pump through a linear mass flow controller. The air sample is passed through a sorbent tube which is a precondensor tube which aborbs agent from the measured air sample. After sampling, a control system terminates flow of sample air and initiates a flow of dry nitrogen through the precondensor tube and at the same time activates a precondensor preheater. The rapid heating of the precondensor tube causes very rapid desorption of agent which flows with the nitrogen carrier gas into the GC column to be sorbed once again. As the GC column is heated, the agent moves through the column to elute at a time dependent on column design and heating ramp selected. Here it is detected with a flame photometric detector (fpd) equipped with either a sulfur or phosphorus emission filter, depending on agent being used. The detector ignores all detector peaks except those which exist during a short window that is centered on the elution time for the agent being used. The computer provides a record of the peak along with digital printouts of peak height and peak area within the selected area.

Measurements are made by placing the test article, in the test cell to simulate the environmental conditions for safe operation and measuring the rate at which agent vapors accumulate in the test cell. This is accomplished by a sequence of agent concentration measurements in the chamber and application of the expression $$V\frac{dC}{dt} = \frac{dm}{dt} = [S(t) - L(t)] \qquad \text{Equation 1}$$

where V is the volume of the test cell, C the agent concentration as a function of time, t. S(t) is the offgassing rate, i.e., the rate at which agent vapors enter the chamber by desorption from the test article, and L(t) is the loss rate of agent from the chamber due to ventilation of. the test cell and sorption of agent vapor on the test cell.

The ideal offgassing test procedure requires ventilation of the offgassing chamber at a rate that would provide a flow speed of one meter per second over the test article. The evaporation rate, p, of a free liquid to the atmosphere is given by $$p = F(v)(e_s - e_A)$$

where $e_s$ and $e_A$ are respectively the saturation and ambient vapor pressures of the liquid and F(v) is an empirical function of wind speed. For a given vapor pressure difference the limiting factor for evaporation rate is the thickness of the thin air layer above the liquid surface in which transport of the vapor is determined by molecular diffusion.

The mass transport rate through this layer is given by $$\frac{dm}{dt} = E\frac{de}{dz} = E\frac{e_s - e_A}{h}$$

where E is the molecular diffusion coefficient, de/dz is the vapor pressure gradient, and h is the thickness of the laminar boundary layer. The thickness of the laminar boundary layer decreases as windspeed and turbulence above that layer increase and, as a consequence, evaporation rate increases. F(v) accounts for that relationship. Thus, assuming that some free liquid is present on the surface of the test article, it is ideally important to reproduce wind speeds that correspond to desired values which are determined to be desirable under the circumstances by the skilled artisan. When the evaporating material is not a free liquid, i.e., when the material is sorbed onto or into the substrate, the limiting factor in vapor production is not the thickness of the molecular diffusion layer. Instead vapor production is limited by the short range forces that bond the adhering materials to the substrate and by the diffusion rate from within the substrate to the offgassing surface. Offgassing continues for many hours after all free liquid would have evaporated under the prevailing conditions, and in other cases in which offgassing rate increases with time after decontamination of the article is complete. While the ideal situation is to reproduce field conditions in the laboratory, it is not essential to reproduce those conditions when it can be expected with reasonable certainty that free liquid surfaces do not exist. Preferably, for large items that will be exposed to the external environment, wind speed should be maintained as close as reasonably possible to 1 m/sec, with values greater than 10 cm/sec highly desirable and below 1 cm/sec unacceptable.

In designing the offgassing measurement system it is important to maintain a realistic partial pressure of desorbed vapor such that the difference between saturation and ambient vapor densities may be realistically simulated. Over small pools of liquid agent such as may exist after decontamination, the vapor concentration will always be a fraction of one percent of saturated vapor pressure when wind speed is 1 m/sec. It is necessary therefore that the chamber ventilation rate be maintained at a level that assures similar values within the chamber. With this assured, the same air may be recirculated over the test article several times in order to maintain the desired wind speed.

For proper interpretation of data, it is necessary to account for the loss rate, L(t) in equation 1, throughout the experiment. This may be done by using the equipment configuration of FIG. 2. Referring to FIG. 2, agent laden air is fed to the test cell. The orifice acts as a choke to limit the air flow rate to a desired value such that a known number of liters per minute of agent laden air flows. A portion is diverted to the MiniCAMS for analysis and the balance is vented to a hood. A vacuum pump draws the required agent laden air through the equipment. Total loss rate of agent is the sum of the rate of removal of agent by ventilation of the cell and of the sorption of agent on the walls of the test cell and related plumbing as shown. Thus, $$L(t) = RC + KC \qquad \text{Equation 2}$$

where R is the ventilation rate, C is the instantaneous agent concentration in the test cell, and K, the sorption coefficient, is a constant, relating sorption to concentration. To solve equation 1 for S(t) the source strength, it is necessary to determine K in advance. To determine the sorption coefficient, the equipment is operated in the configuration illustrated in FIG. 2, in which the empty test cell is ventilated with agent laden air at known concentration, $C_o$. Equation 1 then becomes $$V\frac{dC}{dt} = R\,C_o - (RC + KC) \qquad \text{Equation 3}$$

Within a few air exchanges, i.e., t=infinity, in the rigorous solution to equation 1, dC/dt vanishes, so that K can be determined.

$$K = \frac{R(C_o - C)}{C} \qquad \text{Equation 4}$$

The data obtained from the offgassing experiment consists of a sequence of values of concentration, $C(t_i)$ at known times, $t_i$. Thus, equation 5

$$S(t) = V\frac{dc}{dt} + C(R - K) \qquad \text{Equation 5}$$

can be rewritten in terms of the finite time intervals as follows $$\overline{S(t_i - t_{i-1})} = \frac{C(t_i) - C(t_{i-1})}{t_i - t_{i-1}}\,V + \frac{C(t_i) - C(t_{i-1})}{2}\,(R + K)$$

where the left term is the average source strength over the time interval for any given item tested. The test cell and analysis method accurately simulates the ideal field condition without precisely reproducing it in the laboratory, and permits accurate, safe, economical testing of small and medium size objects.

While this invention has been described with reference to the within preferred embodiment and drawings, it is not to be limited thereby, and the invention is to be construed in accordance with the appended claims.

What is claimed is:

1. A cell for measuring gases emitted by a test article which comprises
   (a) a hollow, enclosed, gas impermeable chamber having side walls terminating at a closed end and a gas transfer end, which gas transfer end is capable of receiving and emitting a flow of a ventilation gas therethrough;
   (b) a platform positioned in said chamber and extending from the closed end to the gas transfer end defining a first chamber portion including a first gas transfer end portion, and a second chamber portion including a second gas transfer end portion, said platform having an opening therethrough at a location proximate to the closed end of the chamber;
   (c) means for fixing a test article through the platform such that part of the test article is positioned and exposed within the first chamber portion and another part of the test article is positioned and exposed within the second chamber portion; and
   (d) means for continuously moving a gas into the first gas transfer end portion, through the first chamber portion, over that part of the test article exposed within the first chamber portion, through the platform opening proximate to the closed end of the chamber, through the second chamber portion, over that part of the test article exposed within the second chamber portion, and out the second gas transfer end portion.

2. The cell of claim 1 further comprising means for evaluating gas effluent from the second gas transfer end portion.

3. The cell of claim 1 wherein the gas comprises air.

4. The cell of claim 1 comprising means for continuously recirculating gas from the second gas transfer portion back to the first gas transfer portion.

5. The cell of claim 4 wherein the means for continuously recirculating the gas comprises a fan positioned through the platform between the first chamber portion and the second chamber portion.

6. The cell of claim 1 comprising means for injecting a gas into the first gas transfer portion and removing a gas from the second gas transfer portion.

7. The cell of claim 1 wherein the platform is planar and substantially bisects the chamber.

8. The cell of claim 1 wherein the side walls are cylindrical.

9. The cell of claim 1 wherein the side walls which extend from the closed end are cylindrical for a distance, after which they are conical to the gas transfer end, and wherein the platform comprises two separate, mating plate portions, a first plate portion positioned within the cylindrical side walls and a second plate portion positioned within the conical walls.

10. The cell of claim 1 comprising a gas inlet port through the first gas transfer end portion and a gas outlet port through the second gas transfer end portion.

11. The cell of claim 1 further comprising means for measuring the volumetric flow rate past each side of the platform.

12. The cell of claim 1 wherein the platform is comprised of stainless steel.

13. The cell of claim 1 wherein the gas comprises air; the means for continuously moving a gas comprises a planar fan positioned through the platform between the first chamber portion and the second chamber portion; wherein the platform is planar and comprises stainless steel and substantially bisects the chamber; wherein the side walls which extend from the closed end are cylindrical for a distance, after which they are conical to the gas transfer end; further comprising a gas inlet port through the first gas transfer end portion and a gas outlet port through the second gas transfer end portion; and further comprising means for measuring the volumetric flow rate past each side of the planar platform.

14. A method for measuring gases emitted by a test article which comprises:
   (i) providing a test cell which comprises
      (a) a hollow, enclosed, gas impermeable chamber having side walls terminating at a closed end and a gas transfer end, which gas transfer end is capable of receiving and emitting a flow of a gas therethrough;
      (b) a platform positioned in said chamber and extending from the closed end to the gas transfer end defining a first chamber portion including a first gas transfer end portion, and a second chamber portion including a second gas transfer end portion, said platform having an opening therethrough at a location proximate to the closed end of the chamber;
      (c) means for fixing a test article through the platform such that part of the test article is positioned and exposed within the first chamber portion and another part of the test article is positioned and exposed within the second chamber portion; and
      (d) means for continuously moving a gas into the first gas transfer end portion, through the first chamber portion, over that part of the test article exposed within the first chamber portion, through the platform opening proximate to the closed end of the chamber, through the second chamber portion, over that part of the test article exposed within the second chamber portion, and out the second gas transfer end portion;
   (ii) continuously moving a gas into the first gas transfer end portion, through the first chamber portion, over that part of the test article exposed within the first chamber portion, through the platform opening proximate to the closed end of the chamber, through the second chamber portion, over that part of the test article exposed within the second chamber portion, and out the second gas transfer end portion; and (iii) evaluating the gas effluent from the second gas transfer end.

15. The method of claim 14 wherein the gas comprises air.

16. The method of claim 14 comprising continuously recirculating gas from the second gas transfer portion back to the first gas transfer portion.

17. The method of claim 16 comprising fan means positioned through the platform between the first chamber portion and the second chamber portion for continuously recirculating the gas.

18. The method of claim 14 wherein gas flows from a gas inlet port through the first gas transfer end portion and a gas outlet port through the second gas transfer end portion.

19. The method of claim 14 wherein gas flows over the test article at a rate of about 1 meter/second.

* * * * *